United States Patent
Evitt et al.

(10) Patent No.: US 6,806,394 B2
(45) Date of Patent: Oct. 19, 2004

(54) ECONOMICAL PURIFICATION OF BISPHENOL A

(75) Inventors: Steven D. Evitt, Somerville, MA (US); Dave P. Palmer, Katy, TX (US)

(73) Assignee: Stone & Webster, Inc., Houston, TX (US)

( * ) Notice: Subject to any disclaimer, the term of this patent is extended or adjusted under 35 U.S.C. 154(b) by 37 days.

(21) Appl. No.: 10/415,428

(22) PCT Filed: Nov. 14, 2001

(86) PCT No.: PCT/US01/44249

§ 371 (c)(1),
(2), (4) Date: Sep. 29, 2003

(87) PCT Pub. No.: WO02/40435

PCT Pub. Date: May 23, 2002

(65) Prior Publication Data

US 2004/0044254 A1 Mar. 4, 2004

Related U.S. Application Data

(60) Provisional application No. 60/249,306, filed on Nov. 16, 2000.

(51) Int. Cl.$^7$ ................................................ C07C 39/16
(52) U.S. Cl. .......................................................... 568/728
(58) Field of Search .......................................... 568/728

(56) References Cited

U.S. PATENT DOCUMENTS

| | | |
|---|---|---|
| 4,942,265 A | 7/1990 | Iimuro et al. |
| 5,345,000 A | 9/1994 | Moriya et al. |
| 5,399,784 A | 3/1995 | Asaoka et al. |

*Primary Examiner*—Michael L. Shippen
(74) *Attorney, Agent, or Firm*—Hedman & Costigan, P.C.

(57) ABSTRACT

Process and related apparatus are disclosed for economically producing a very high quality bisphenol A product by a multistage crystallization process utilizing a new cross-flow wash design whereby a high purity wash phenol stream is fed to every washing stage, optionally also in combination with a modified stream flow/recycle design which avoids increased by product production and yield losses otherwise expected from processing increased volumes of wash phenol.

26 Claims, 2 Drawing Sheets

ECONOMICAL PURIFICATION OF BISPHENOL A

This application claims the benefit of Provisional Application No. 60/249,306, filed Nov. 16, 2000.

FIELD OF THE INVENTION

P, P Bisphenol A (BPA) is a commercially significant compound used to manufacture polycarbonates and epoxy resins. The polycarbonate application in particular demands high purity BPA due to stringent requirements for optical clarity and color in the finished application. Accordingly those skilled in the art continually strive to improve the product quality of bisphenol A in economically efficient process schemes. This invention concerns a new process scheme to purify bisphenol A via adduct crystallization.

BACKGROUND OF THE INVENTION

To understand this invention it is first necessary to understand the prior art for BPA, which includes U.S. Pat. No. 4,950,805 (Iimuro, et al.) and U.S. Pat. No. 5,345,000 (Moriya et al.), which patents are incorporated herein by reference.

BPA is formed by the condensation of two moles of phenol with one mole of acetone under acidic conditions. The reaction may take place in the presence of a strong homogenous acid, such as hydrochloric acid, sulfur acid, or toluene sulfonic acid, or in the presence of a heterogeneous acid catalyst, such as a sulfonated ion exchange resin. The reaction may take place in the absence or presence of a thiol promoter, such as a mercaptan, which may be homogeneous in the reaction mixture or fixed to a heterogeneous catalyst A stoichiometric excess of phenol is employed to improve selectivity to the highly desired p,p'-BPA isomer. The crude reaction effluent stream thus contains not only unconsumed phenol, p,p'-BPA and water byproduct from the condensation reaction, but also contains undesirable BPA isomers and impurities, such as the o,p-BPA isomer, trisphenols, codimers, spiroindanes, and colored impurities as well as unreacted acetone, homogeneous acid catalysts, and thiol promoters. Those skilled in the art of producing BPA, recognize that regardless of the method of reacting acetone and phenol to produce BPA, it is necessary to purify the crude reaction effluent stream to obtain a BPA product that is useful for the manufacture of polycarbonates and other engineering thermoplastics.

A conventional practice in the purification of bisphenol A can be generically described by reference to FIG. 1.

Acetone feed to reaction (1) is either makeup acetone (21) or a combination of makeup acetone and unreacted recycle acetone (23) recovered from the downstream distillation system (2). Phenol feed to the reaction consists of distilled phenol (22) from the downstream distillation section (2) or phenol recycle (24) produced as the liquid separation or wash product from the downstream solid/liquid separation (4), and typically contains a large quantity of impurities and BPA, or a combination of these two streams. Stream (22) may in some cases be combined with the acetone recycle stream 23. The reaction system effluent (25) is sent to a distillation system (2), which recovers unreacted acetone (23), phenol (22) and waste streams, such as the wastewater of condensation (40). These lighter fractions are separated from the reactor effluent stream to form a concentrated BPA stream (26), which still contains a large quantity of phenol.

In the adduct crystallization technology that is widely practiced, for example in U.S. Pat. No. 4,927,978, U.S. Pat. No. 4,950,805 and U.S. Pat. No. 5,345,000, sufficient cooling of the concentrated BPA and phenol stream produces a crystalline adduct which comprises one molecule of phenol and one molecule of the desired p,p'-BPA isomer. This crystallization is a relatively efficient way to purify p,p'-BPA from the other isomers and impurities contained in the stream. The crystallization, depending on purity requirements and economic considerations, can be conducted in a selected number of multiple stages, with each stage producing a much higher purity adduct crystal. Each crystallization stage may consist of a single crystallizer or a multitude of crystallizers in series. The preferred number of crystallizers per stage is between 1 and 3. The number of crystallization stages may be any number greater than or equal to two. For illustration purposes in FIG. 1, three stages of crystallization (3, 5 and 7) are indicated. The effluent (27) from the first crystallization stage (3) is sent to a solid-liquid separation device (4). These devices can use hardware well known to those skilled in the art, such as filters or centrifuges. A key feature in all of these systems is to first separate the bulk of the liquid to produce a solids crystal cake and a mother liquor (filtrate/centrate) stream, and then to wash the cake to remove impurities. Phenol is typically used to effect this wash, and the ultimate product quality is strongly determined by the purity of the washing agent. Phenol is a useful washing agent to the extent that it does not introduce new impurities into the BPA-phenol adduct crystal.

The solid-liquid separation devices (4, 6 and 8) produce an adduct stream (respectively 35, 36, 37) and one or more liquid streams containing some mixture of spent wash and/or filtrate/centrate (e.g., 28, 33, 34, 54, 53). For the purposes of adduct dissolution, crystal recovery, and for the enhancement of crystallization and material flow, those skilled in the art will typically recycle some or all of each of the mother liquor and wash effluent streams from one separation stage back to the preceding crystallization stage (e.g., 33, 34).

The adduct produced from each stage may be placed in a phenol solution again and recrystallized to afford additional purification. The final adduct (37) is sent to the BPA finishing apparatus (9), wherein a liquid state phenol is vaporized in some fashion away from BPA to produce a high purity molten BPA product (51). The clean phenol (38) so produced can be combined with the makeup phenol to the plant (50) to provide a solvent (52) for washing the solid adduct crystals produced in, at least, the last solid-liquid separation (8).

It is known to those skilled in the art that an efficient means to produce a high purity product through multi-stage crystallization is to send the cleanest wash liquid to the final stage, and in turn send some combination of filtrate/centrate or spent wash from each stage as wash (53, 54) to the immediate upstream stage. Such a scheme effectively minimizes the phenol requirements for the overall crystallization wash system, and uses the cleanest phenol where it is most necessary, i.e., in the final stage. This wash scheme is usually referred to as a counter-current wash flow.

The total liquid (28) recovered from the first stage solid/liquid separation (4), a combination of mother liquor and wash effluent, is recirculated to the condensation reactor system (1). Optionally a stream (29), consisting of all or a portion of the recycle liquid (28), may be sent to a recovery system (10) which rearranges unwanted heavy byproducts contained in the recycle liquid to useful precursors of BPA or to BPA itself A waste stream (32) is removed, and the improved stream (30) is returned to the recycle liquid. Some of the recycle liquid (31) may bypass the recovery system (10). The combined streams (30) and (31) are used as a reactor feed stream (24).

SUMMARY OF THE INVENTION

By contrast, in the present invention, as illustrated in FIG. 2, the washing scheme is changed in order to provide an even higher purity product, and to accomplish this beneficial result without compromising the yields of raw materials to product. In addition, other process modifications shown in FIG. 2 and described below cooperate synergistically with the modified wash scheme to achieve unexpectedly enhanced results.

In accordance with the present invention, it has now been found that an extremely high quality BPA product can be produced by co-feeding a clean or substantially clean phenol stream to every stage of washing. This type of washing is herein referred to as a cross-flow wash system. While generally counter-current wash flow maximizes product purity for a given quantity of wash supply, in some processes, particularly crystallization, where impurities are bound in the crystal product at each stage, and, therefore, cannot be washed out, we have found that increased product purity can be obtained by using a cross-flow wash system in accordance with this invention as long as an increased wash supply can readily be made available. With the prior art BPA processes, however, wash flows were limited to the amount of fresh and recovered phenol (e.g., 50, 38 in FIG. 1) because the use of additional phenol from other sources within the plant would degrade plant yields. Higher quantities of wash in the conventional counter-current flow schemes create increased flow of recycle liquor back to the condensation reactor, and the raw material consumption of the overall process worsens. Moreover, the amount of BPA lost in the purge (32) also increases due to a combination of a higher make of impurities in the reactor as well as a more dilute mother liquor stream with respect to impurities but not p,p'-BPA For these reasons, no one of ordinary skill in this art based on existing knowledge and experience with conventional BPA processes would be led to try to employ higher quantities of wash in conjunction with counter-current flow.

In the present invention, however, a new approach is disclosed for integrating the process operations to provide a purer product without suffering from expected yield losses. This invention is described by reference to FIG. 2. FIG. 2 shows the utilization of the same overall unit operations as seen in FIG. 1, where the same or comparable elements are indicated by the same reference numbers, but the integration between these blocks is substantially different. The following description points out the key differences between this scheme (FIG. 2) and the prior art (FIG. 1).

DETAILED DESCRIPTION OF PREFERRED EMBODIMENTS

Figure 2:
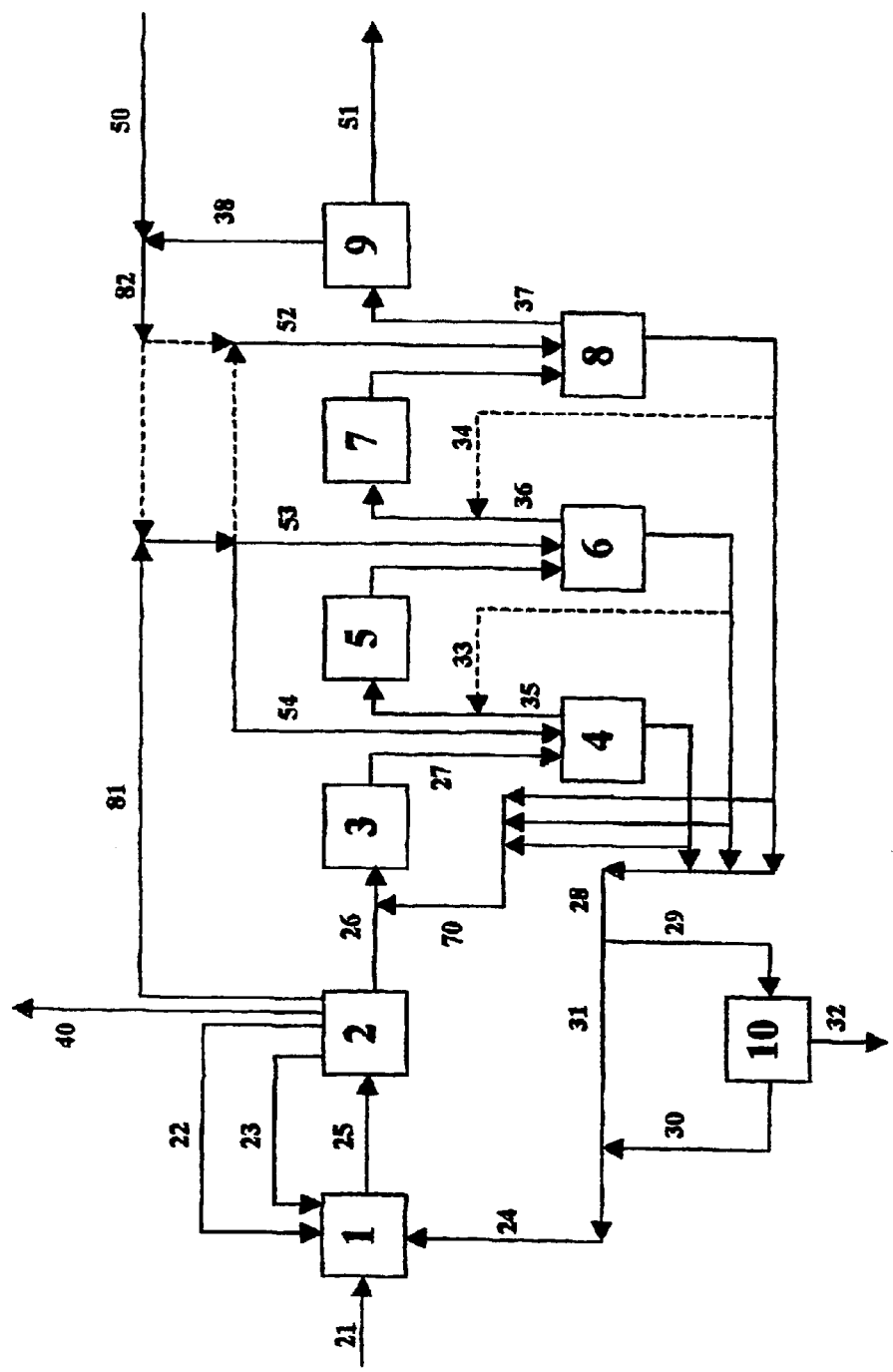
FIG. 2 is an illustrative process flow diagram of a preferred embodiment of a BPA process in accordance with the present invention.

As shown in FIG. 2, in accordance with the present invention the wash (54, 53, 52) supplied to the staged solids/liquid separation systems (blocks 4, 6 and 8) now flows in a cross-flow scheme. As a result of this design modification, the wash to each stage now contains only a high purity phenol, with high purity composition being fed to each stage. The high purity phenol is supplied to blocks 4, 6 and 8 via streams 54, 53 and 52 respectively. Some of this high purity phenol (82) is supplied from a combination of fresh makeup phenol to the plant (stream 50) and phenol recovered from the high purity adduct in the finishing system 9 (stream 38). In order to obtain sufficient quantities of such high purity phenol to maintain adequate wash rates for the multiple solids/liquid separation devices, the BPA process of the present invention introduces a new source of high purity phenol, namely stream 81, which is recovered from the distillation section (2). Alternatively, utility costs can be reduced by producing a slightly less pure phenol in the distillation section (2), and feeding his wash (81) only to the upstream crystallization stages (4 and 6 in FIG. 2), while feeding the fresh and recovered phenol (82) of somewhat higher purity only to the last downstream crystallization stage (8 in FIG. 2).

Figure 1:
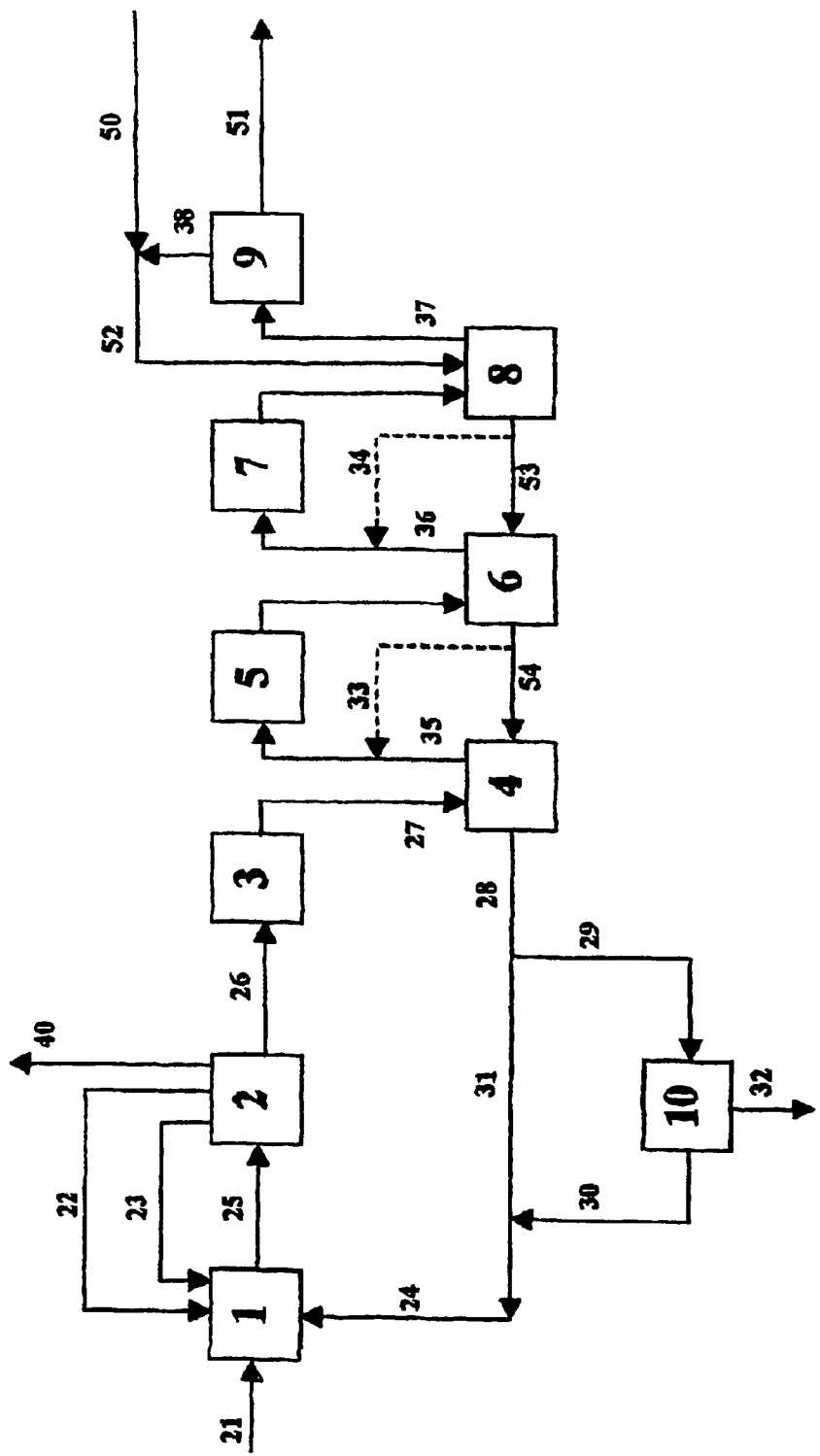
FIG. 1 is a representative process flow diagram of BPA production according to one common conventional technology.

By material balance, the net quantity of recycle liquid (28) leaving the first separation stage (4 in FIG. 2) must be larger under such a scheme than with the process shown in FIG. 1. This higher phenol flow, which will be saturated with BPA, results in more BPA content in the feed to the condensation reaction system 1, as all the flow is returned to the reactor system, leading to increased byproduct make in the reactors which ordinarily would be expected to result in a loss in yield.

In this invention, however, it is proposed to avoid this high recycle phenol flow. The additional high purity wash phenol (81) will be generated in the distillation section (2) by removing phenol from the crystallizer feed stream (26). In the prior art BPA process, this modification would have expected to lead to problems in the crystallizer, since phenol and BPA concentrations in the feed stream (26) are optimized for crystallizer performance. In this invention, by contrast, it has been found that these problems can be completely or substantially avoided by immediately diluting stream 26 with a phenol flow (70) obtained selectively from the wash effluent and mother liquor flows from the crystallization stages. This step of the present invention is therefore another key distinction from the prior art BPA processes. By material balance it can be shown that when the flow of the dilution stream (70) substantially equals the flow of the new high purity phenol supply (81), there is substantially no increase in the recycle liquid (28) returning to the condensation reactors from the separation section.

Furthermore, the present invention may also include the step of creating the dilution stream (70) by selectively taking, as needed, part or all of the wash effluent and mother liquor streams of the separation stages (4, 6, 8) starting with the last stage, to create a stream containing the least amount of impurities. In a preferred embodiment of the present invention, the purity of the final product is enhanced if stream 70 is drawn so as to contain a minimum of impurities. Therefore, it will preferentially be made up of, in order of preference, flow from the wash effluent, then from the mother liquor of the last separation stage, then by adding flows from the wash effluent, and then from the mother liquor of each preceding separation stage, until the desired volume of flow is achieved.

It will be apparent to those skilled in the art that other changes and modifications may be made in the above-described apparatus and methods for economical purification of bisphenol A without departing from the scope of the invention described herein, and it is intended that all matter contained in the above description shall be interpreted in an illustrative and not a limiting sense.

What is claimed is:

1. A process for producing and purifying p,p'-bisphenol A comprising the steps of:
   (a) reacting acetone with a stoichiometric excess of phenol under acidic conditions to form a reaction product stream consisting essentially of crude p,p'-bisphenol A product, unreacted phenol, possibly unreacted acetone, water of condensation, and other reaction byproducts;
   (b) distilling the reaction product stream from step (a) to distill off a volatilized unreacted phenol stream, possibly an unreacted acetone stream, and the water of condensation, while sending a BPA liquid feed stream consisting essentially of concentrated bisphenol A together with remaining unreacted phenol and higher boiling point reaction byproducts downstream to a multistage phenol adduct crystallization and purification process;
   (c) producing first-stage phenol adduct crystals by crystallization in the crystallization step of the first of at least two in-series BPA purification stages, each comprising a crystallization step and a solid-liquid separation and wash step;
   (d) washing the first-stage phenol adduct crystals with a high purity wash phenol stream, which includes at least a portion of the volatilized unreacted phenol stream recovered from step (b), said wash phenol stream being substantially free of bisphenol isomers and other impurities, to produce first-stage washed phenol adduct, first-stage spent wash, and first-stage mother liquor;
   (e) sending the first-stage washed phenol adduct to a second purification stage for producing second-stage phenol adduct crystals; and,
   (f) washing the second-stage phenol adduct crystals with a high purity wash phenol stream which is substantially free of bisphenol isomers and other impurities to produce second-stage washed phenol adduct, second-stage spent wash, and second-stage mother liquor.

2. A process according to claim 1 further wherein the wash phenol stream used to wash the second-stage phenol adduct crystals includes at least a portion of the unreacted phenol stream recovered from the distillation of step (b).

3. A process according to claim 1 comprising the further steps of:
   (g) sending the second-stage washed phenol adduct to a third purification stage for producing third-stage phenol adduct crystals; and,
   (h) washing the third-stage phenol adduct crystals with a high purity wash phenol stream which is substantially free of bisphenol isomers and other impurities to product third-stage washed phenol adduct, third-stage spent wash, and third-stage mother liquor.

4. A process according to claim 3 further wherein the wash phenol stream used to wash the third-stage phenol adduct crystals includes at least a portion of the unreacted phenol stream recovered from the distillation of step (b).

5. A process according to claim 3 further wherein the wash phenol streams used to wash the second-stage phenol adduct crystals and the third-stage phenol adduct crystals each include at least a portion of the unreacted phenol stream recovered from the distillation of step (b).

6. A process according to any of claims 1–5 comprising the further step of dewatering the phenol adduct crystals from each crystallization step before washing them with said high purity wash phenol stream.

7. A process according to any of claims 1–5 further wherein the BPA liquid feed stream from step (b) comprises about 30–60% by weight of p,p'-BPA.

8. A process according to any of claims 1–5 further wherein the BPA liquid feed stream from step (b) comprises about 30–55% by weight of p,p'-BPA.

9. A process according to any of claims 1–5 further comprising the step of recycling a first portion of spent wash, separated mother liquor, or both from at least one of said purification stages to mix with the BPA liquid feed stream from step (b) to reduce the concentration of p,p'-BPA in the feed to the first purification stage to below 40% by weight.

10. A process according to any of claims 1–5 further comprising the step of recycling a first portion of spent wash, separated mother liquor, or both from at least one of said purification stages to mix with the BPA liquid feed stream from step (b) to reduce the concentration of p,p'-BPA in the feed to the first purification stage to about 25–40% by weight.

11. A process according to claim 9 further comprising the step of recycling a second portion of said spent wash, separated mother liquor, or both to the crystallization step of the first purification stage.

12. A process according to claim 11 wherein a part of said second portion is recycled to each of the crystallizers which comprise the crystallization step of the first purification stage.

13. A process according to claim 11 further comprising the step of recycling remaining spent wash and separated mother liquor to reaction step (a).

14. A process according to claim 1 further wherein the high purity wash phenol streams used to wash the first-stage and second-stage phenol adduct crystals include fresh makeup phenol to the process.

15. A process according to claim 1 further comprising a downstream step of devolatilizing bisphenol A-phenol adduct recovered from the final solid/liquid separation step to produce phenol and a molten bisphenol A product stream.

16. A process according to claim 15 further wherein the high purity wash phenol streams used to wash the first-stage and second-stage phenol adduct crystals include at least a portion of the phenol produced in said downstream step of devolatilizing bisphenol A-phenol adduct.

17. A process according to any of claims 1–5 further wherein said volatilized unreacted phenol stream originates from a condensation reactor.

18. A process according to claim 11 wherein a predominant proportion of spent wash from the first solid-liquid separation and wash step is recycled to the crystallization step of the first purification stage.

19. A process according to any of claims 1–5 further wherein phenol adduct crystals produced in at least the final downstream purification stage are washed with fresh makeup phenol fed to the process, or with phenol produced from a finishing step for obtaining a final bisphenol A adduct product, or a mixture thereof.

20. A process according to claim 19 wherein phenol adduct crystals produced in the first purification stage are washed with phenol produced from phenol-containing effluents produced in the bisphenol A process.

21. A process according to claim 20 further comprising the step of dewatering the phenol adduct crystals from each crystallization step before washing them with said high purity wash phenol stream.

22. A process according to claim 11 further wherein a higher proportion of the spent wash is recycled to the crystallization step of the first purification stage relative to the proportion of mother liquor that is thus recycled.

23. A process for the purification of bisphenol A via adduct crystallization of phenol adduct from a phenol solution in a multistage process wherein the adduct crystals from each of multiple purification stages are separated from the mother liquor, dewatered, and washed with a wash phenol stream substantially free of bisphenol isomers and impurities which includes an unreacted phenol stream recovered from an upstream reaction stage.

24. A process according to claim 23 wherein the wash phenol stream includes makeup phenol to the process.

25. A process according to claim 23 wherein the wash phenol stream includes phenol produced from the finishing of bisphenol A-phenol adduct.

26. A process according to claim 23 wherein adduct from purification stages downstream from the first purification stage is washed with makeup phenol to the process, phenol produced from the finishing of bisphenol A-phenol adduct, or both, and adduct from the first purification stage is washed with a phenol produced from upstream phenol-containing process streams.

* * * * *